United States Patent [19]

Dinsmore et al.

[11] 4,446,105

[45] May 1, 1984

[54] SYSTEM FOR ANALYZING COAL LIQUEFACTION PRODUCTS

[75] Inventors: Stanley R. Dinsmore, Norris; John E. Mrochek, Oak Ridge, both of Tenn.

[73] Assignee: The United States of America as represented by the United States Department of Energy, Washington, D.C.

[21] Appl. No.: 437,782

[22] Filed: Oct. 29, 1982

[51] Int. Cl.³ ............................................. G01N 31/08
[52] U.S. Cl. ................................. 422/70; 73/61.1 C; 210/96.1; 210/198.2; 210/659; 436/140; 436/150; 436/161
[58] Field of Search .................. 422/70; 436/140, 150, 436/161; 210/96.1, 198.2, 659; 73/61.1 C

[56] References Cited

U.S. PATENT DOCUMENTS

| | | | |
|---|---|---|---|
| 3,508,880 | 4/1970 | Hrdina | 210/659 |
| 4,154,583 | 5/1979 | Favre et al. | 210/659 |
| 4,233,156 | 11/1980 | Tsukada et al. | 73/61.1 C |
| 4,271,697 | 6/1981 | Mowery, Jr. | 73/61.1 C |
| 4,379,751 | 4/1983 | Yoritomi et al. | 210/659 |

OTHER PUBLICATIONS

The Role of HPLC and LC-MS in the Separation and Characterization of Coal Liquefaction Products, Dark et al, Journal of Chromatographic Science, vol. 16, Jul. 1978, pp. 289-293.
Chemically Bonded Aminosilane Stationary Phase for the HPLC Separation of Polynuclear Aromatic Compounds, Wise et al, Analytical Chem., vol. 49, No. 14, Dec. 1977, pp. 2306-2310.
Use of Liquid Chromatography in the Characterization of Asphalts, Dark et al, Journal of Chromatographic Science, vol. 16, Dec. 1978, pp. 610-615.

Primary Examiner—Michael S. Marcus
Attorney, Agent, or Firm—Edwin D. Grant; Stephen D. Hamel; Michael F. Esposito

[57] ABSTRACT

A system for analyzing constituents of coal-derived materials comprises three adsorption columns and a flow-control arrangement which permits separation of both aromatic and polar hydrocarbons by use of two eluent streams.

4 Claims, 4 Drawing Figures

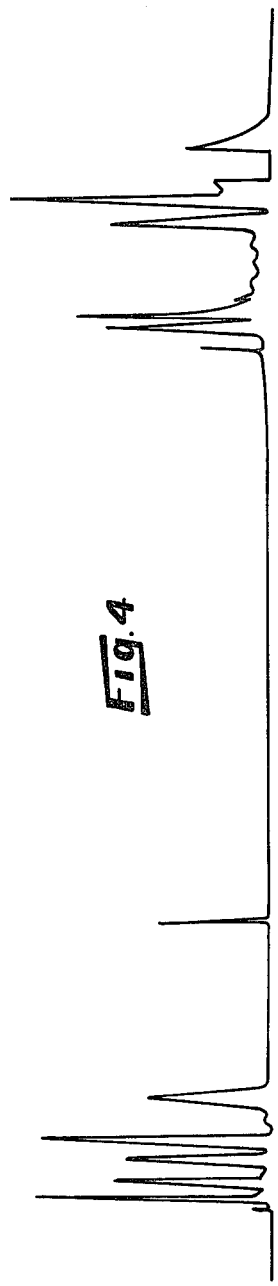

… …

SYSTEM FOR ANALYZING COAL LIQUEFACTION PRODUCTS

This invention, which was made under a contract with the United States Department of Energy, relates to a liquid chromatography system and, more particularly, to a system which can advantageously be used to identify hydrocarbon components of fuels produced by liquefaction of coal.

BACKGROUND OF THE INVENTION

A typical chromatographic separation scheme which has been used heretofore for analyzing components of coal-derived liquids includes two adsorption columns which separate saturated and aromatic hydrocarbons from polar hydrocarbons, elutes and characterizes the aromatics, and then elutes the polar compounds as a single fraction by backflushing of the columns. The subsequent steps required to analyze constituents of the single fraction of polar compounds in separate apparatus are both time-consuming and conducive to the introduction of errors in the case of small samples.

SUMMARY OF THE INVENTION

It is therefore an object of this invention to provide an analytical system for rapidly and efficiently identifying constituents of coal liquefaction products.

Another object of the invention is to provide an integrated liquid chromatography system wherein aromatic compounds are separated according to number of rings and polar compounds are separated according to their functionality.

These objects are accomplished by a preferred embodiment of the invention wherein a column-switching arrangement (1) introduces a test sample into a first column where both aromatic and polar hydrocarbons are adsorbed on a packing, (2) elutes the aromatic hydrocarbons from said packing with a stream of hexane into a second column where the aromatics are separated according to ring number, the polar fraction being retained in the first column, (3) directs the stream of hexane from the second column to detecting means for characterization of the aromatics, (4) backflushes the first and second columns by reversing the flowing stream of hexane, (5) elutes the polar fraction, by means of a gradient solution containing hexane, chloroform and acetic acid, from the first column to a third column where the polar hydrocarbons are separated according to functionality, and (6) directs the stream of gradient solution containing the separated polar hydrocarbons to the detecting means for characterization of said polar hydrocarbons.

DESCRIPTION OF THE DRAWINGS

FIG. 4 is an optical spectrogram of a hydrocarbon sample chromatographically analyzed by means of the preferred embodiment.

DESCRIPTION OF THE PREFERRED EMBODIMENT OF THE INVENTION

Figure 1:
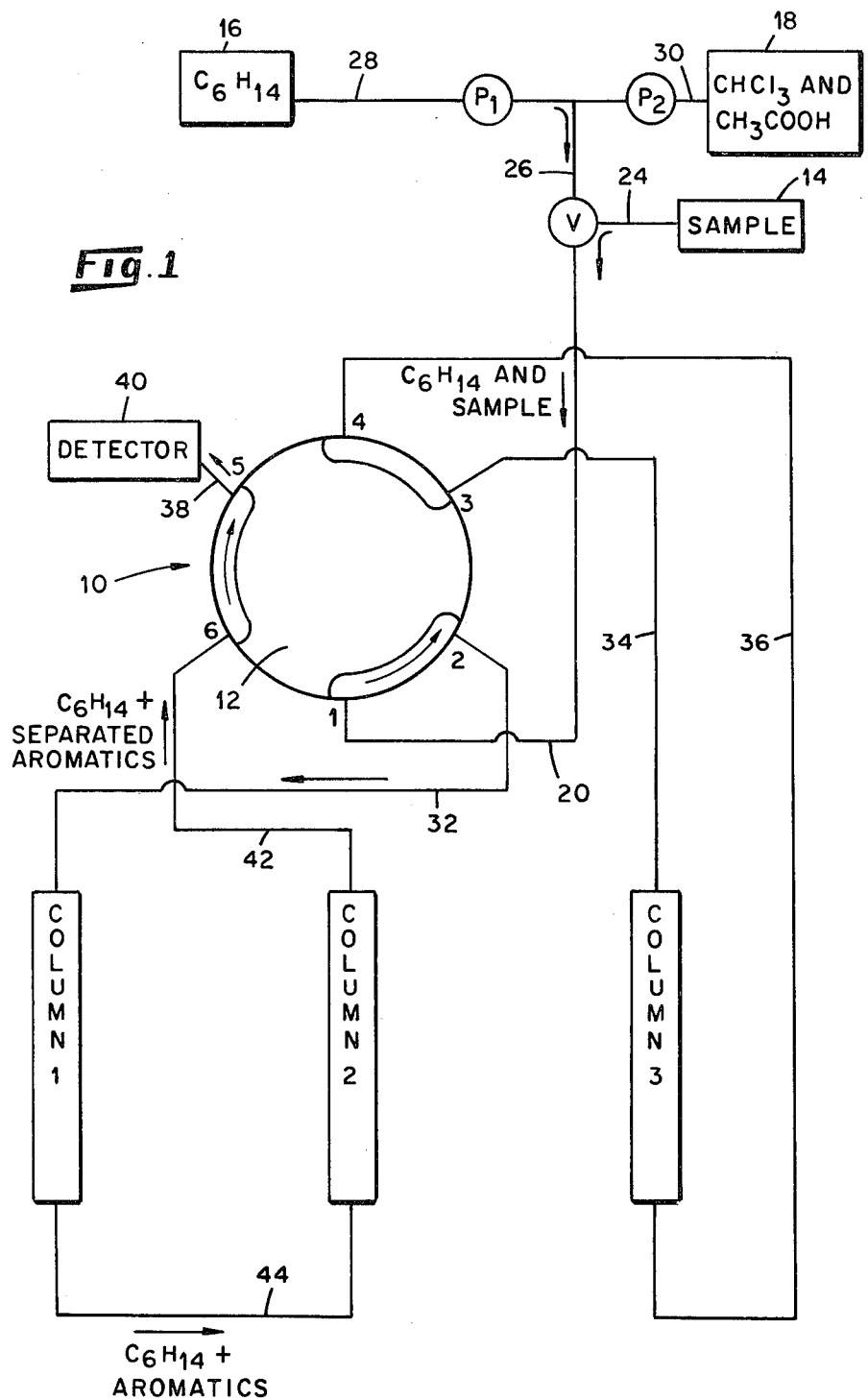
FIG. 1 is a schematic representation of a preferred embodiment of the invention, illustrating the flow of sample-containing stream of hexane through two columns thereof during a first phase of operation.

Columns 1, 2 and 3 of the preferred embodiment of the invention are vertically extending tubes of the type used in chromatographic separation apparatus and their thickness to length ratio is exaggerated in the drawings. Schematically illustrated in cross section in the drawings and generally designated therein by reference number 10 is a valve having six ports 1 through 6 and a rotary gate 12 which can be turned to place each of these ports in communication with either of the pair of ports adjacent thereto through grooves formed in the gate. Port 1 of valve 10 is connected to a sample injector 14, a container 16 holding hexane, and a container 18 holding a solution of chloroform and 0.5% by volume acetic acid by means of first conduit means which includes (1) a conduit 20 extending between said port 1 and the outlet of a sample injection valve V, (2) a first branch conduit 24 extending between valve V and sample injector 14, (3) a conduit 26 connected to valve V, (4) a conduit 28 connected to conduit 26 and container 16 and provided with a metering pump $P_1$, and (5) a conduit 30 connected to conduit 26 and container 18 and provided with a metering pump $P_2$. A second conduit means 32 connects port 2 of valve 10 to the upper end of column 1, and port 3 is connected by a third conduit means 34 to the upper end of column 3 while the lower end of the same column is connected to port 4 by a fourth conduit means 36. A fifth conduit means 38 connects port 5 to a detector means 40, and a sixth conduit means 42 connects port 6 to the upper end of column 2 while the lower end of the same column is connected to the lower end of column 1 by a seventh conduit means 44.

In the preferred embodiment of the invention, column 1 is packed with a first adsorbent consisting of aminopropylsilane bonded to $10\mu$ silica particles, column 2 is packed with a second adsorbent consisting of octadecylsilane bonded to $10\mu$ silica particles, and column 3 is packed with a third adsorbent consisting of cyano groups functionally bonded to $10\mu$ silica particles. Detector means 40 is preferably an ultraviolet spectrometer but can be any other means capable of identifying components of a mixture of hydrocarbon compounds.

OPERATION OF THE PREFERRED EMBODIMENT OF THE INVENTION

Figure 2:
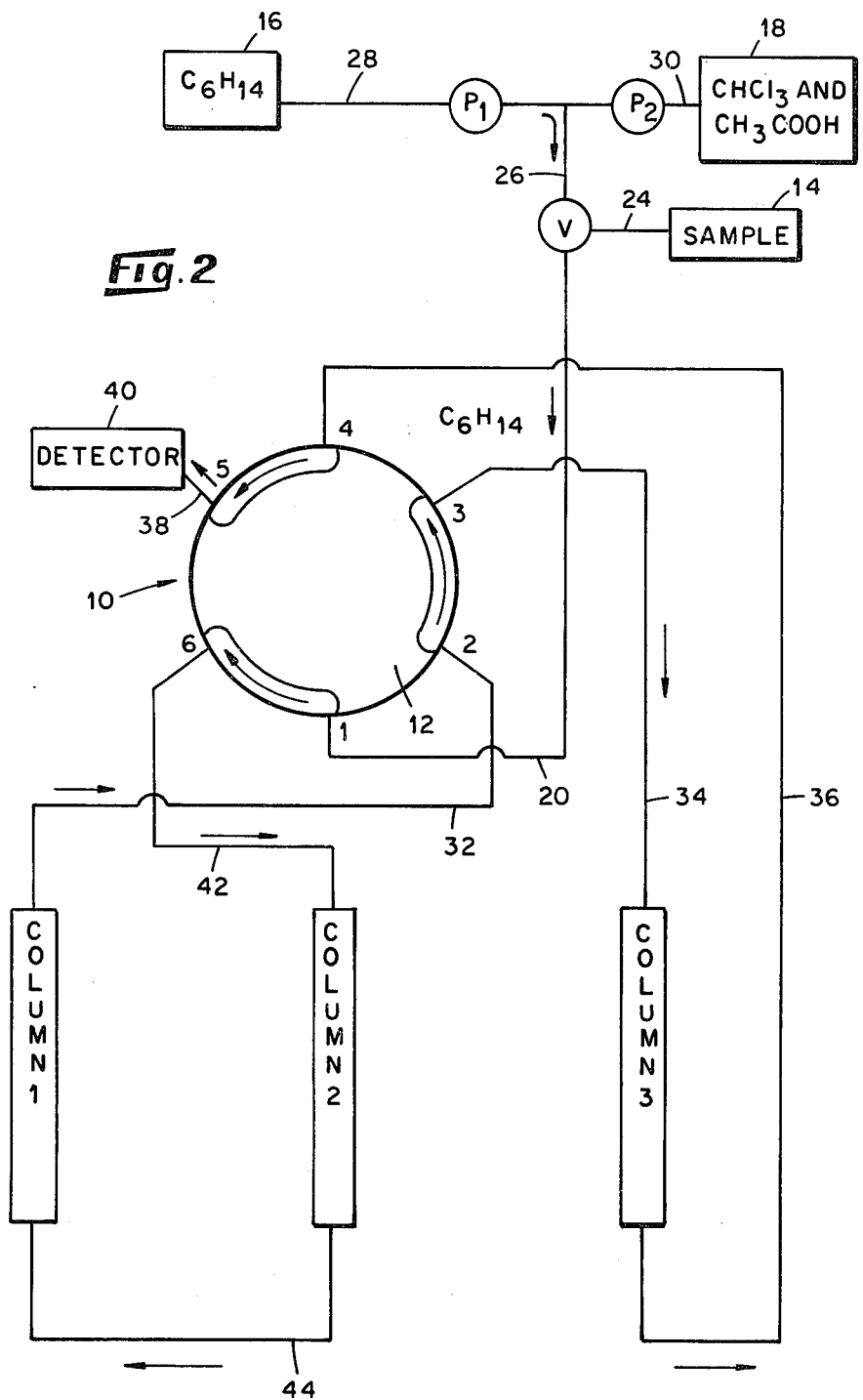
FIG. 2 illustrates flow of a flushing stream of hexane through the aforesaid two columns and a third column during a second phase of operation.
Figure 3:
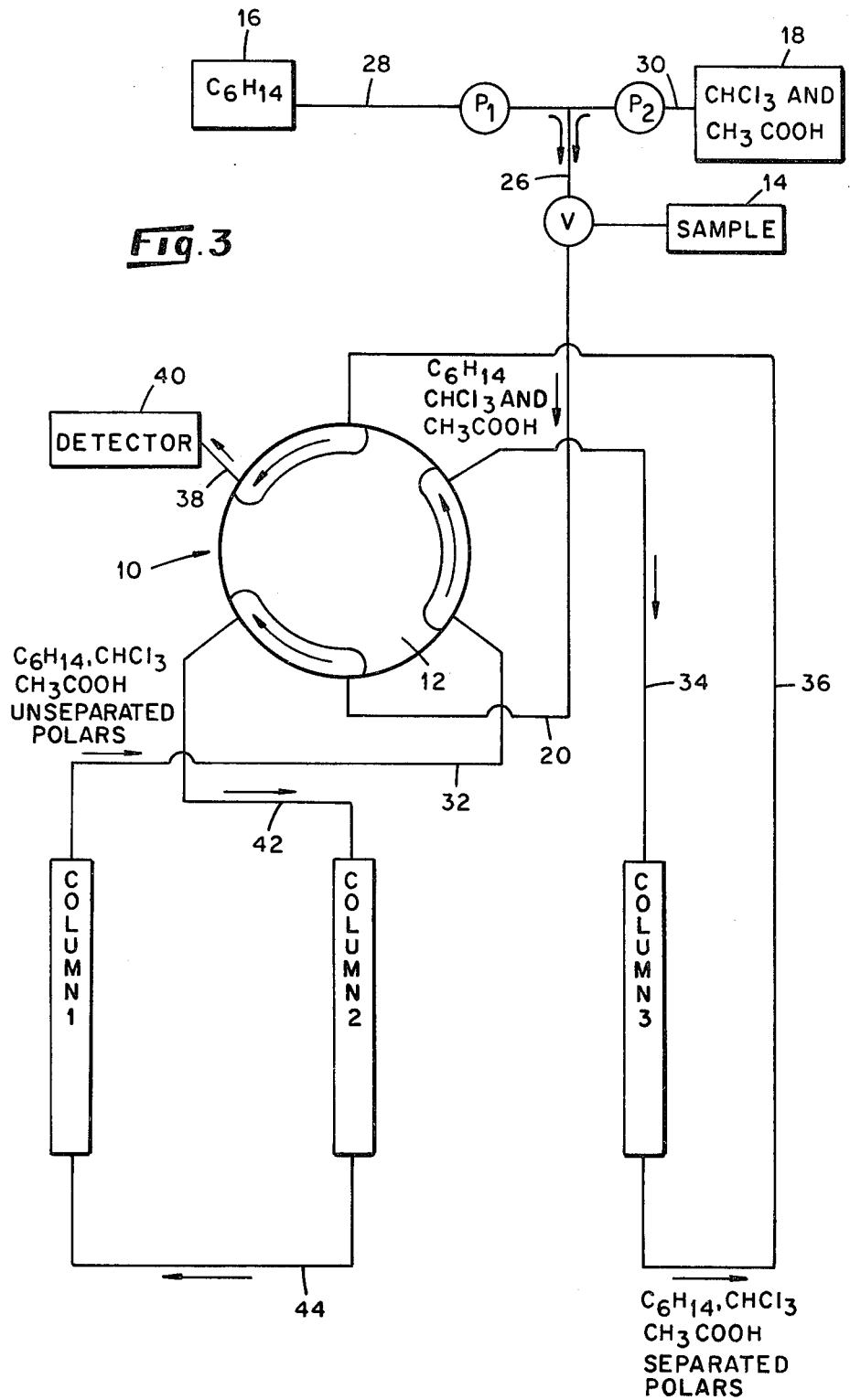
FIG. 3 illustrates flow of a gradient stream through the three columns during a third phase of operation.

The 280 nm ultraviolet spectrogram of a coal-derived hydrocarbon fuel sample which is illustrated in FIG. 4 was obtained by using the above-described apparatus in the following manner. With metering pump $P_2$ off and gate 12 of valve 10 turned to the position illustrated in FIG. 1, valve V was adjusted and pump $P_1$ was operated so that a stream consisting of the hydrocarbon fuel sample from sample injector 14 and hexane from container 16 flowed for 15 minutes through conduit 20 to port 1 of valve 10, out of port 2 of valve 10 and through conduit 32 into the upper end of column 1, out of the lower end of column 1 and through conduit 44 into the lower end of column 2, out of the upper end of column 2 and through conduit 42 to port 6 of valve 10, and finally out of port 5 of valve 10 and through conduit 38 to detector 40. During this time, aromatic compounds were differentially desorbed from the adsorbents in columns 1 and 2 and thereby separated by ring number in the stream flowing therethrough while polar compounds were retained in the upper portion of column 1, peaks of the aromatics being at the left in FIG. 4. After the aromatics were separated annd identified in detecting means 40, gate 12 of valve 10 was turned to the position illustrated in FIG. 2, and pump $P_1$ was operated so that hexane was pumped through conduit 20 to port 1 of valve 10, out of port 6 of valve 10 and through conduit 42 into the upper end of column 2, out of the lower end of column 2 and through conduit 44 into the lower end of column 1, out of the upper end of column 1 and through conduit 32 to port 2 of valve 10, out of port 3 of valve 10 and through conduit 34 into the upper end of column 3, out of the lower end of column 3 and through conduit 36 to port 4 of valve 10, and finally out of port 5 of valve 10 and through conduit 38 to detector 40. This flow of hexane in the reverse direction through columns 1 and 2, relative to the flow of the mixture for hexane and sample therethrough, was continued for 5 minutes to transfer the polar compounds from the top of column 1 to the top of column 3 containing the cyanopropylsilane packing. Metering pump $P_2$ was then gradually activated and metering pump $P_1$ gradually inactivated by automatic means, with gate 12 of valve 10 remaining in the same position, so that a gradient stream flowed through columns 1–3 in the same direction as described for the hexane flush stream, the gradient stream going from 100% hexane to 100% of the solution of chloroform and 0.5% acetic acid in 20 minutes using a concave gradient curve. This flow was maintained for an additional 20 minutes. During this period of operation, which is illustrated in FIG. 3, the polar compounds retained in column 1 were stripped from the adsorbent in column 1 and then adsorbed and differentially desorbed from the adsorbent in column 3 and thereby separated in the gradient stream. Peaks of polars are at the right in FIG. 4.

The arrangement of the disclosed system permits the separation and characterization of aromatic and polar compounds in a heretofore unavailable chromatographic analysis, thereby providing a more rapid and efficient means for evaluating coal-derived liquids.

What is claimed is:

1. A system for analyzing components of a liquid sample containing a plurality of both aromatic and polar hydrocarbons, comprising:

detecting means for identifying said aromatic and polar hydrocarbons;

a first column containing a first adsorbent which adsorbs said aromatic and polar hydrocarbons;

a second column containing a second adsorbent which adsorbs said aromatic hydrocarbons;

a third column containing a third adsorbent which adsorbs said polar hydrocarbons, said first, second and third adsorbents differing chemically from one another, means for introducing said sample into said first column, whereupon said aromatic and polar hydrocarbons therein are adsorbed on said first adsorbent;

means defining and providing a source of first eluent capable of differentially desorbing said aromatic hydrocarbons from said first and second adsorbents;

means defining and providing a source of second eluent capable of collectively desorbing said polar hydrocarbons from said first adsorbent and differentially adsorbing said polar hydrocarbons from said third adsorbent; and flow control means for (1) passing a first stream of said first eluent through said first column and thence through said second column and to said detecting means, whereupon the aromatic hydrocarbons are differentially desorbed from said first and second adsorbents and thereby separated in said first stream before passing to said detecting means, while said polar hydrocarbons remain on said first adsorbent, and (2) subsequentially forming and passing a gradient stream comprising a gradually decreasing quantity of said first eluent and a gradually increasing quantity of said second eluent in the reverse direction through said first and second columns, relative to flow of said first stream therethrough, and thence through said third column and to said detecting means, whereupon the polar hydrocarbons adsorbed on said first adsorbent are collectively desorbed therefrom into said second stream and transferred therein to said third column and there differentially desorbed from said third adsorbent and thereby separated in said gradient stream before passing to said detecting means.

2. The system of claim 1 wherein:

said first adsorbent comprises aminopropylsilane bonded to $10\mu$ silica particles;

said second adsorbent comprises octadecylsilane bonded to $10\mu$ silica particles;

said third adsorbent comprises cyano groups functionally bonded to $10\mu$ silica particles;

said first eluent is hexane; and said second eluent is a mixture of chloroform and acetic acid.

3. The system of claim 1 wherein said flow control means is arranged for passing a stream of said first eluent in the reverse direction through said first and second columns, relative to flow of said first stream therethrough, before said gradient stream is passed through said columns.

4. The system of claim 1 wherein said flow control means comprises:

a six-port valve having a rotary gate for selectively placing each of its ports in communication with either of the pair of ports adjacent thereto;

first conduit means connecting a first port of said valve to said sources of first and second eluents and to said means for introducing said sample into said first column;

second conduit means connecting a second port of said valve to one end of said first column;

third conduit means connecting a third port of said valve to one end of said third column;

fourth conduit means connecting a fourth port of said valve to the other end of said third column;

fifth conduit means connecting a fifth port of said valve to said detecting means;

sixth conduit means connecting a sixth port of said valve to one end of said second column; and seventh conduit means connecting the other end of said second column to the other end of said first column.

* * * * *